(12) United States Patent
Ruan et al.

(10) Patent No.: US 10,597,369 B2
(45) Date of Patent: Mar. 24, 2020

(54) MONOSULFONIC PHENYLTETRAZOLE COMPOUNDS WITH APPLICATIONS

(71) Applicant: HANGZHOU JENNIFER BIOTECH CO., LTD., Hangzhou (CN)

(72) Inventors: Benfang Helen Ruan, Hangzhou (CN); Jennifer Jin Ruan, Hangzhou (CN)

(73) Assignee: HANGZHOU JENNIFER BIOTECH CO., LTD., Hangzhou (CN)

( * ) Notice: Subject to any disclaimer, the term of this patent is extended or adjusted under 35 U.S.C. 154(b) by 0 days.

(21) Appl. No.: 15/774,579

(22) PCT Filed: Nov. 9, 2016

(86) PCT No.: PCT/CN2016/105133
§ 371 (c)(1),
(2) Date: May 8, 2018

(87) PCT Pub. No.: WO2017/080443
PCT Pub. Date: May 18, 2017

(65) Prior Publication Data
US 2018/0244637 A1 Aug. 30, 2018

(30) Foreign Application Priority Data

Nov. 9, 2015 (CN) .......................... 2015 1 0757078

(51) Int. Cl.
| | | |
|---|---|---|
| *C07D 257/04* | (2006.01) | |
| *C07D 401/04* | (2006.01) | |
| *C12Q 1/32* | (2006.01) | |
| *C07D 417/04* | (2006.01) | |
| *C07D 405/04* | (2006.01) | |
| *C07D 409/04* | (2006.01) | |
| *C07D 403/04* | (2006.01) | |
| *C07D 413/04* | (2006.01) | |
| *G01N 21/78* | (2006.01) | |

(52) U.S. Cl.
CPC ......... *C07D 257/04* (2013.01); *C07D 401/04* (2013.01); *C07D 403/04* (2013.01); *C07D 405/04* (2013.01); *C07D 409/04* (2013.01); *C07D 413/04* (2013.01); *C07D 417/04* (2013.01); *C12Q 1/32* (2013.01); *G01N 21/78* (2013.01); *G01N 2333/90611* (2013.01); *G01N 2333/90616* (2013.01)

(58) Field of Classification Search
None
See application file for complete search history.

(56) References Cited

U.S. PATENT DOCUMENTS

| 6,063,587 A | 5/2000 | Ishiyama et al. |
| 2007/0111274 A1 | 5/2007 | Fukuoka |

FOREIGN PATENT DOCUMENTS

| CN | 1823049 A | 8/2006 | |
| JP | 55-24103 | * 8/1978 | ........... C07D 257/04 |
| JP | S5524103 A | 2/1980 | |
| JP | S5661367 A | 5/1981 | |
| JP | 2007289096 | 11/2007 | |
| WO | 2004063353 A2 | 7/2004 | |

OTHER PUBLICATIONS

Zhang et al., Analytical Biochemistry, vol. 509, Sep. 15, 2016, pp. 33-40.*
Machine translation of JP 55-24103. Obtained from http://worldwide.espacenet.com. Accessed Apr. 4, 2019.*
First Office Action and Search Report from CN app. No. , dated Aug. 2, 2017, with English translation from Global Dossier.
Third Office Action and Supplemental Search Report from CN app. No. , dated Jul. 9, 2018, with English translation from Global Dossier.
Written Opinion of the International Searching Authority from PCT/CN2016/105133, dated Feb. 8, 2017.
International Search Report from PCT/CN2016/105133, dated Feb. 8, 2017.
International Preliminary Report on Patentability from PCT/CN2016/105133, dated May 15, 2018.
Notification to Grant Patent Right for Invention from CN app. No. 201510757078.2, dated Nov. 19, 2018, with English translation from Global Dossier.
Extended European Search Report from EP app. No. 16863619.9, dated May 3, 2019.

\* cited by examiner

*Primary Examiner* — Alicia L Otton
(74) *Attorney, Agent, or Firm* — Ladas & Parry, LLP

(57) ABSTRACT

A class of compounds of monosulfonic phenyltetrazole, with the structure of 2-(R1 phenyl)-5 (2-sulfonic phenyl)-2H-tetrazole. The 2-sulfonic phenyl tetrazolium salt of this invention has advantages of low toxicity, short synthetic route, easy control of purity and quality. As the 2-sulfonic phenyl tetrazolium salts has almost no absorption at 450 nm where the reduzate has greater absorption, spectrophotometry can simply and rapidly determine the activity of glutamate dehydrogenase, or the content of NADH/NADPH.

1 Claim, 2 Drawing Sheets

MONOSULFONIC PHENYLTETRAZOLE COMPOUNDS WITH APPLICATIONS

CROSS-REFERENCE TO RELATED APPLICATION

This application is the U.S. nation phase of PCT Application PCT/CN2016/105133 filed on Nov. 9, 2016 which claims priority to Chinese application No. 201510757078.2, filed on Nov. 9, 2015, the disclosures of which are incorporated by reference in their entireties.

FILED OF THE INVENTION

This invention relates to the field of pharmaceutical biotechnology, and in particular to a class of compounds of monosulfonic phenyltetrazole with their applications.

BACKGROUND OF THE INVENTION

NADPH and NADH are important redox mediators in organisms. Although the difference of their chemical structure is only one phosphate group, their biological function is significantly different. NADH participates in decomposition reactions and plays an important role in cellular respiration and nutrient metabolism, whereas, NADPH participates in synthetic reactions and is consumed to provide energy for biosynthesis of large molecules. NADPH also plays an important role in cellular defensive oxygen (ROS) injury as a vital component of the intracellular antioxidant defense system. Therefore, accurate quantification of the concentration of NADPH and NADH is important for the detection of biological actions and the diagnosis of diseases.

NADPH and NADH can be detected by the color generated in their redox reactions with tetrazoliun salts. The TTC (2, 3, 5-triphenyltetrazolium salt) was first synthesized in 1894 and is a fat-soluble light-sensitive compound for the detection of seed viability. The MTT assay is another method for detecting cell survival and growth. MTT is reduced to—water-insoluble blue-violet crystalline—formazan by succinate dehydrogenase from living cellular mitochondria, then absorbance can be detected under 540 nm or 720 nm after the formazan is dissolved by DMSO. The assay has advantages of high sensitivity, favorable economic benefit and so forth, but the disadvantage is the need for multiple steps in the detection process. Water-soluble WST (bisulfonic phenyltetrazolium salt) was synthesized in 1997 and used in commercial assays for cell viability. However, water-soluble WST-8 would not be easily synthesized and purified and its purity and quality are difficult to control.

SUMMARY OF THE INVENTION

The objective of this invention is to provide a class of monosulfonic phenyltetrazole compounds of novel structure that are highly sensitive reagents for the detection of NADPH or NADH, and these compounds comprises the structure of formula I:

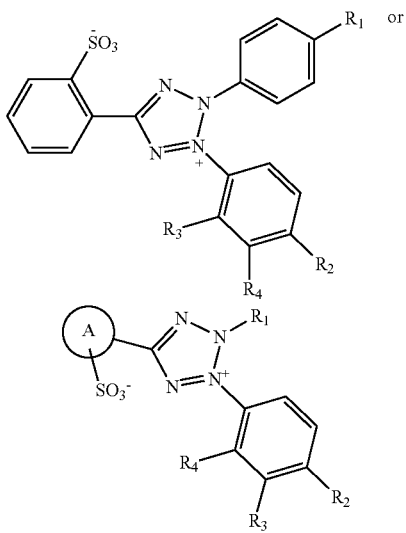

wherein:
$R_1$, $R_2$, $R_3$ and $R_4$ are each independently selected from substituent W or H.

substituent W comprises 1-50 atoms group selected from the group comprising C, H, N, O, S, P, Si and a halogen like F, Cl, Br, I;

also, R1 are substituted & unsubstituted aromatic group or substituted & unsubstituted heterocyclic aromatic groups.

substituent W is selected from the group comprising hydrogen, alkyl, alkoxy, nitro, cyano, carboxyl, halogen, hydroxyl, sulfonamide, amino, substituted alkyl, substituted alkoxy, substituted carboxyl, substituted sulfonamide or substituted amino (the substituents are selected from the group comprising alkyl, aryl, aralkyl), heterocycloalkyl or polycycloalkyl.

A is a monosulfonate containing substituted & unsubstituted aromatic group or substituted & unsubstituted heterocyclic aromatic groups.

This invention also provides a series of monosulfonic phenyltetrazole compounds as shown below: 9. The monosulfonic phenyltetrazole compounds of claim 1, which selected from the following compounds:

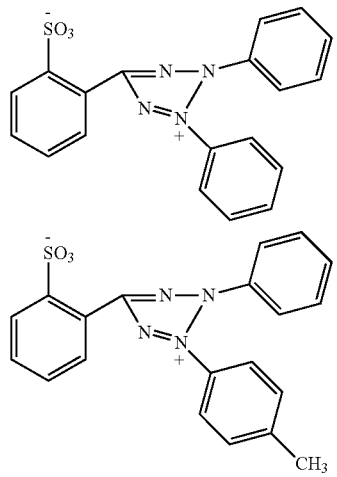

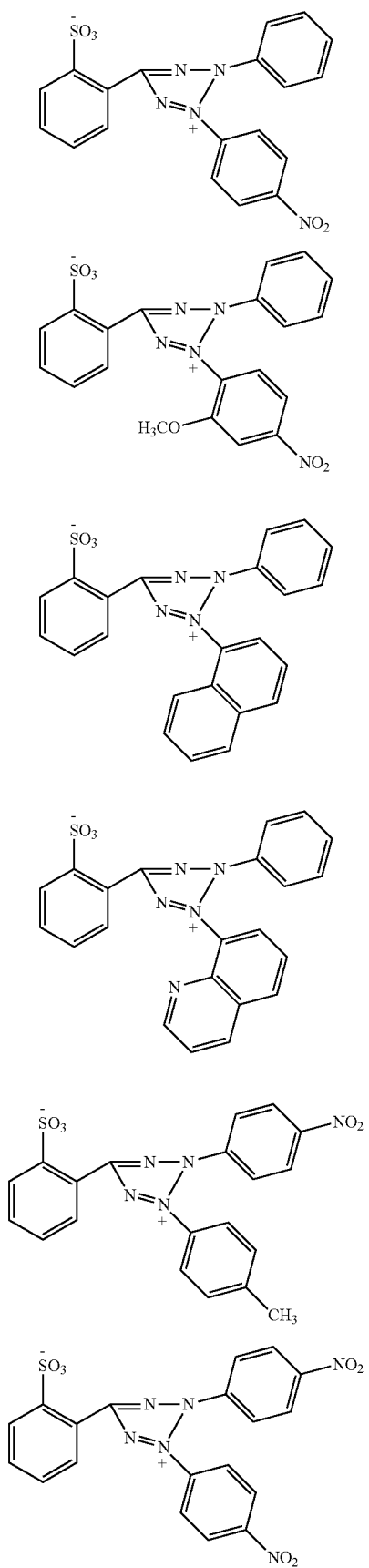
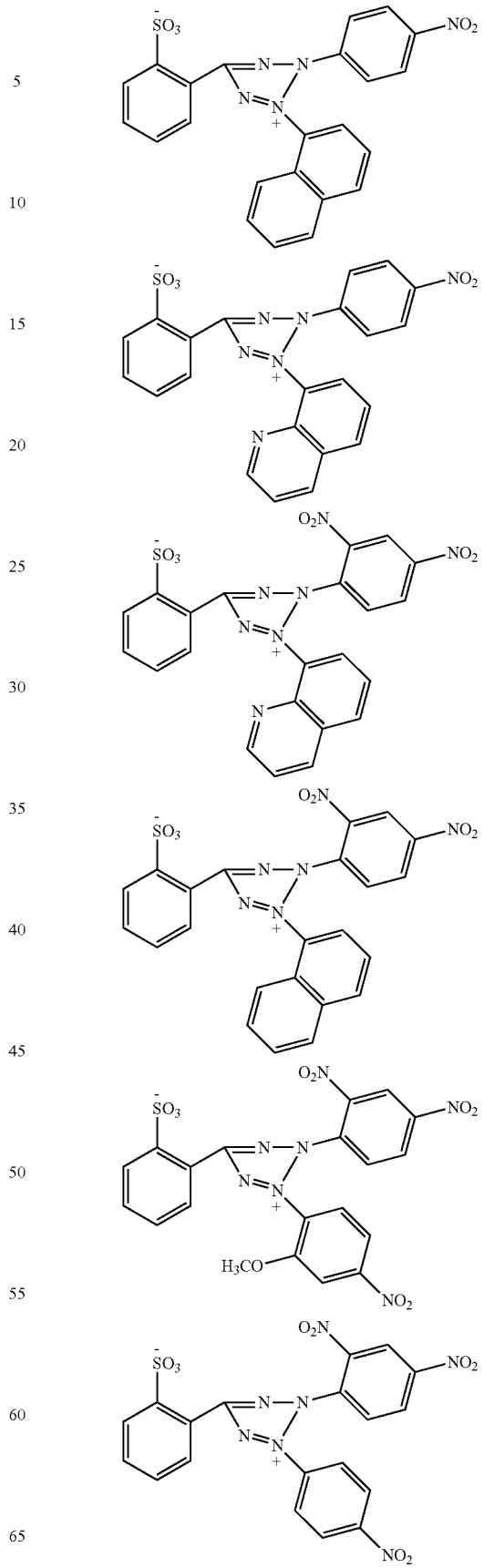

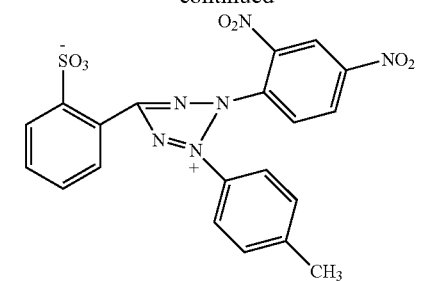
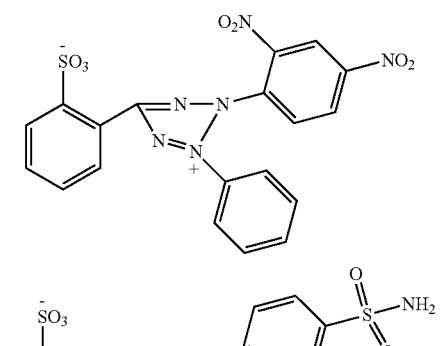
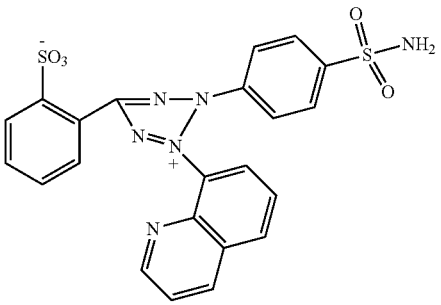
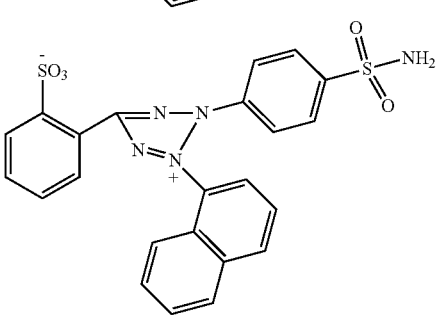
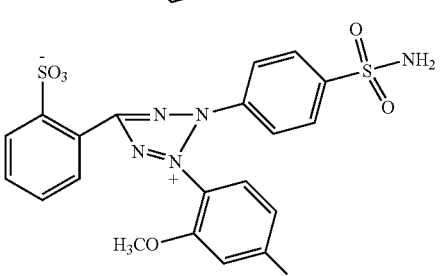
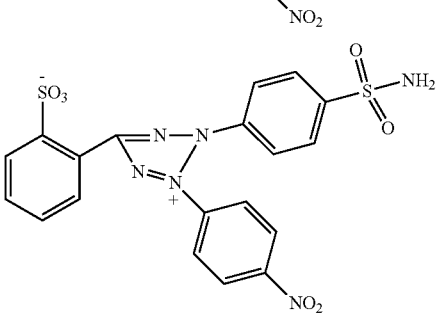
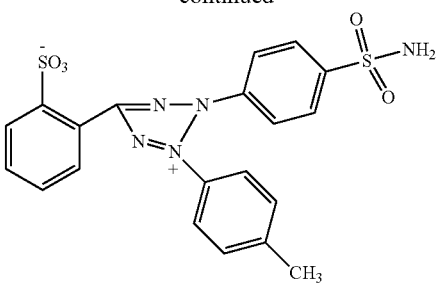
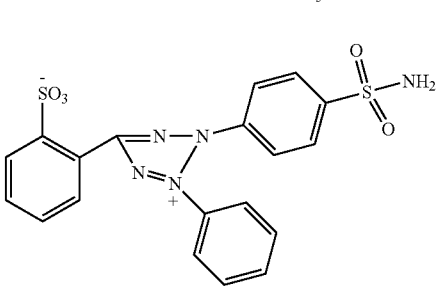
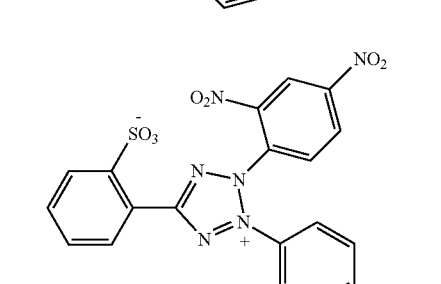
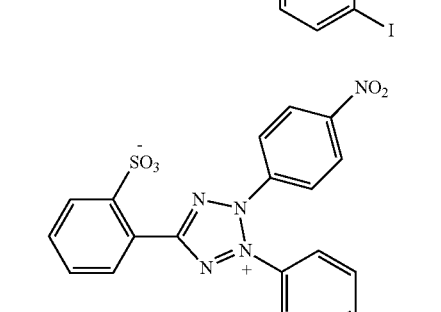
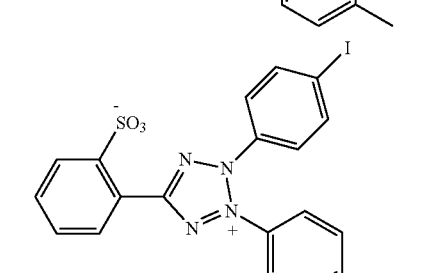
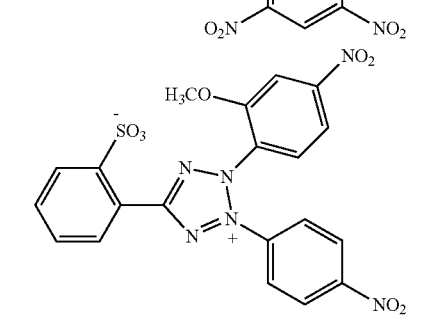

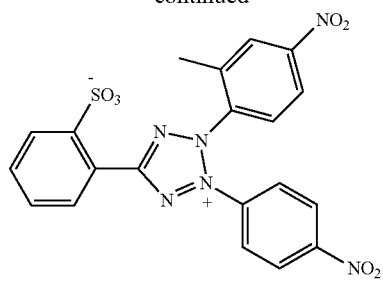
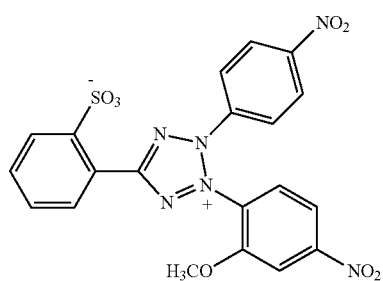
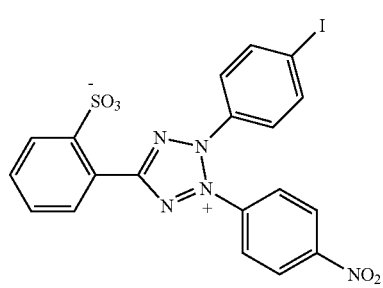
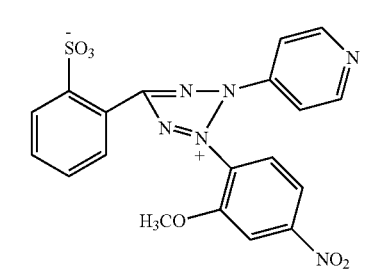
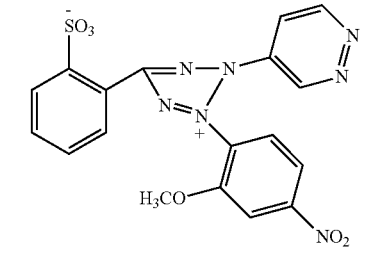
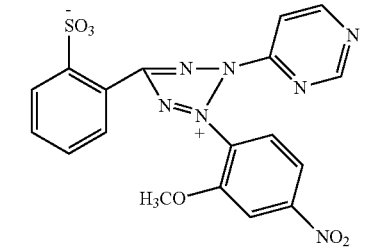
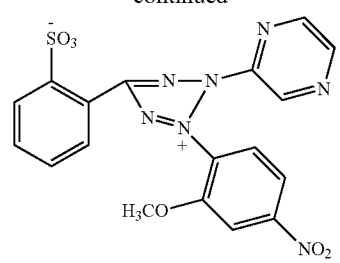
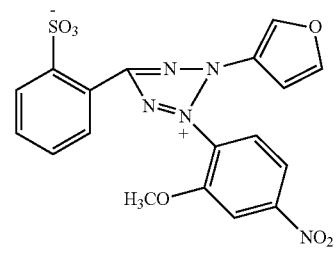
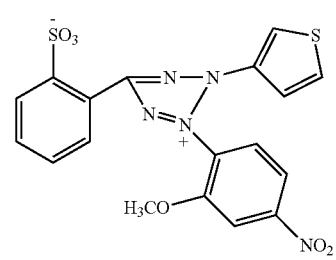
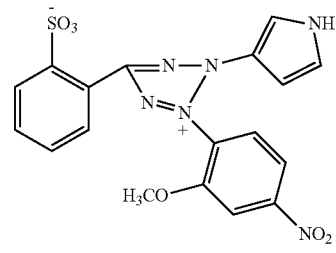
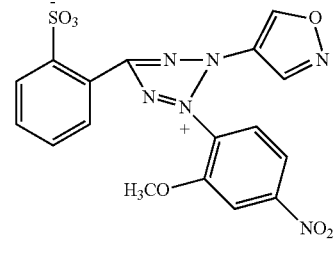
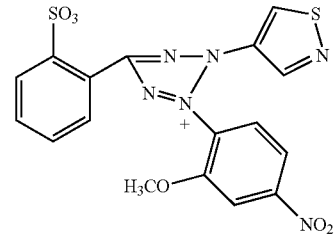

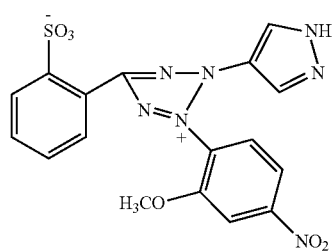
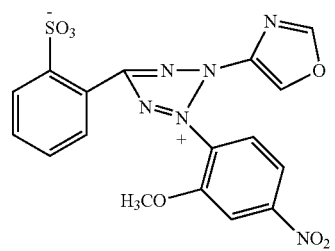
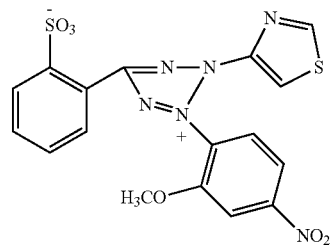
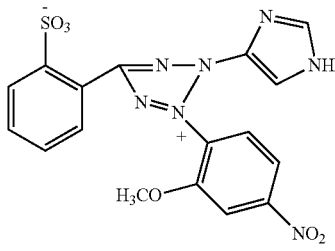
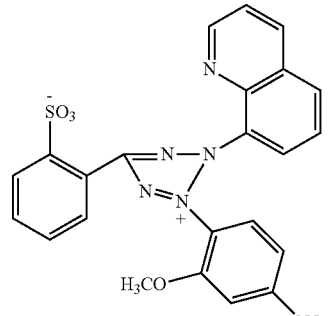
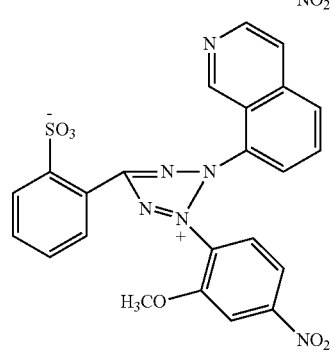
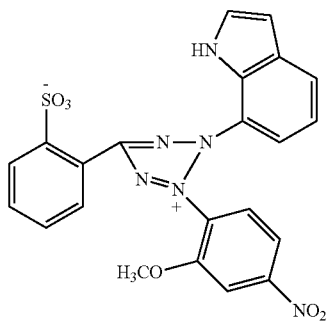
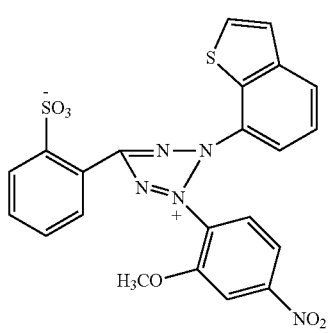
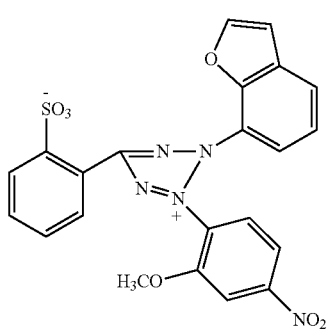
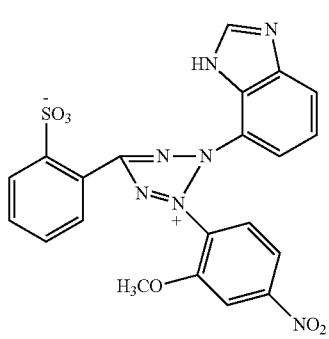
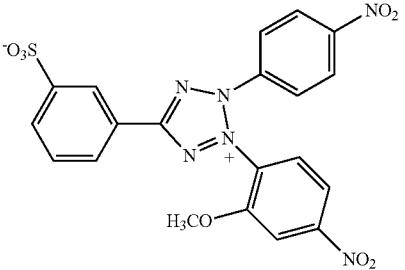

-continued

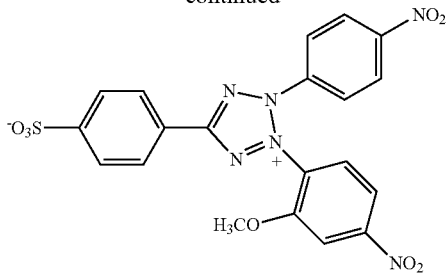

This invention also provides other monosulfonic phenyltetrazole compounds with the structure of formula II:

II

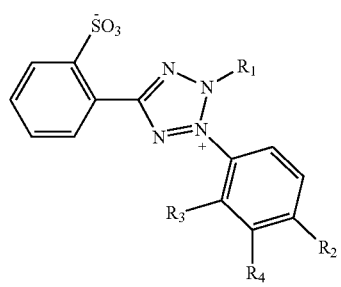

wherein:

$R_1$ is substituent $X_1$ unsubstituted, or substituent $X_1$ substituted with one or more substitutable substituent $X_2$ independently, wherein substituent $X_1$ and/or substituent $X_2$ are selected optionally from the following substituted or unsubstituted groups: phenyl, nitro, sulfonic group, sulfonamide, a halogen, alkoxy, alkyl, 6-membered heterocycloalkyl group containing 1 or 2 N atoms, 5-membered heterocycloalkyl group containing 1 or 2 heteroatoms each independently selected from N, S, O, bicyclic heteroaryl groups containing 1 or 2 heteroatoms selected from N, S, O;

$R_2$, $R_3$ and $R_4$ are each independently selected from substituent Y or H, wherein substituent Y is optionally selected from the following groups: substituted or unsubstituted alkyl, alkoxy, nitro, halogen atom, azo, phenyl, substituted sulfonic group, heterocyclic alkyl containing 1 N substituent, cycloalkyl.

Substituent X, $X_1$, $X_2$ is preferably selected from the group comprising phenyl, nitrophenyl, multi-nitrophenyl, benzenesulfonic group, benzenesulfonamido, halophenyl, methylnitrophenyl, 6-membered heterocycloalkyl containing 1 or 2 N atoms, 5-membered heterocycloalkyl containing 1 or 2 heteroatoms each independently selected from N, S, O, bicyclic heteroaryl containing 1 or 2 heteroatoms selected from N, S, O;

Substituent Y is preferably selected from the group comprising alkyl, nitro, alkoxy, cycloalkyl, heterocycloalkyl containing 1 N atom, nitrophenylazo containing from 1 to 3 nitro, benzenesulfonicazo group, and alkoxy nitrophenyl group;

Also substituent X, $X_1$, $X_2$ is preferably selected from the group comprising phenyl, 5-membered heterocyclic ring or 6-membered heterocyclic ring—with an optional number of sulfonic group or sulfonamide substituents;

In addition, the benzenesulfonic group of the formula I or formula II of this application may be further modified, and the sulfonic group can be in the meta or para position of the phenyl;

The monosulfonic phenyltetrazole compounds of this invention should consist of all isomers expressed by the formula I and II. Without respect to enantiomers and diastercoisomers of each structural formula, the present invention contains R and S stereoisomers for an asymmetric center, as well as Z and E double-bond isomers, as well as Z and E conformational isomers.

Furthermore, the monosulfonic phenyltetrazole compounds of this invention also comprise the salts produced by the compounds of formula I and formula II. Such salts preferably contain alkali salts or alkaline-earth salts, but not limited to sodium salt, potassium and calcium salt.

Another object of this invention is to provide the application of monosulfonic phenyltetrazole compounds, for the determination of activity of glutamate dehydrogenase and glutaminase, or for the content determination of NADPH/NADH in cells, like 1) determining of NADPH/NADH level, 2) various dehydrogenase enzyme activity, 3) serum dehydrogenase level and/or 4) cell viability.

This invention has significant technical improvement as followed:

The phenyltetrazolium salt of this invention overcomes the high toxicity of the traditional fat-soluble tetrazolium salt and has an advantage of low toxicity; meanwhile, unlike the difficult synthesis and purification of the water-soluble tetrazolium salt, the phenyltetrazolium salt has merits of short synthetic route, easy control of purity and quality. As the tetrazolium salt almost has no absorption at 450 nm where the reduced form—formazan has greater absorption, spectrophotometry can simply and rapidly determine the activity of glutamate dehydrogenase, or the content of NADH in cells. In addition, because of its water solubility, the assay can be followed continuously using a spectrometry. Also, it is more stable than WST-8, and does not react with many antioxidants; therefore, it is more suitable for compound screening.

BRIEF DESCRIPTION OF DRAWINGS

The invention is accompanied by seven Drawings, wherein.

EXAMPLES

Figure 1:
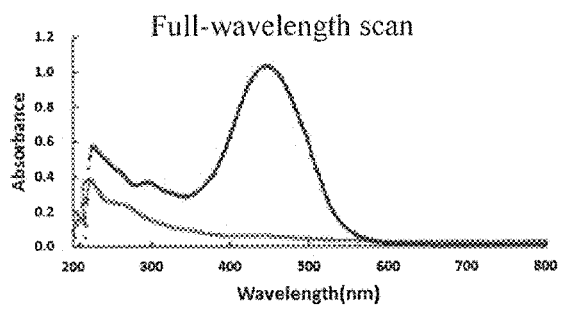
FIG. 1 shows the full-wavelength scanning curve of a compound (tetrazolium) with weak UV absorbance around 450 nm, and its reduced-phenyl compound (formazan) with has strong UV absorbance around 450 nm. All compounds we claim showed strong UV absorbance different between its tetrazolium form and formazan form.

Throughout this specification and in the claims that follow, the following terms are defined with the following meanings, unless explicitly stated otherwise.

The terms in present invention, if not specifically defined, take their ordinary meanings as would be understood by those skilled in the art.

The term "halogen" refers to halogen substituents from the group including fluoro (—F), chloro (—Cl), bromo (—Br), or iodo (—I); The term "halogenation" describes the above halogen substituents as substitutes for hydrogen in a compound.

The term "alkyl" refers to straight-/branched-chain and cyclic saturated aliphatic hydrocarbon groups. It includes groups with single bond, such as methyl, ethyl, propyl, isopropyl, butyl, primary/secondary/tertiary butyl, cyclopropyl, methylcyclopropyl, cyclobutyl; as well as alkyl groups with two or more free bonds but still meeting the valence-bond theory, such as —CH$_2$—, —(CH$_2$)$_2$—, —(CH$_2$)$_3$—, —(CH$_2$)$_4$—, —C(CH$_3$)(CH$_2$)$_2$—.

The term "alkoxy" refers to the OR group, where R is a variety of alkyl groups, such as various straight chain, straight-/branched-chain alkyl and cycloalkyl groups.

The term "cyano" refers to a functional group or substituent comprising a carbon atom and a nitrogen atom linked through a triple bond.

The term "substitute" describes the hydrogen atom of group is replaced by other functional group or substituent.

The term "polynitrophenyl" describes at least two hydrogen atoms on phenyl are replaced by nitro and positions of substituted hydrogen can be chosen arbitrarily, such as para, meta and ortho.

The term "methylnitrophenyl" refers to a functional group or substituent obtained by substituting two hydrogen atoms on the phenyl with a methyl and a nitro, and positions of methyl and nitro can be arbitrarily selected.

The term "multi-nitrophenyl" refers to mono-substituted, double-substituted, or multi-substituted substituent or group wherein one or more nitro substituents at any proper position of group of phenol.

The term "benzenesulfonic group" refers to substituent or group comprising benzene sulfonic acid.

The term "halophenyl" refer to mono-substituted, double-substituted or multi-substituted phenylat any proper position.

The term "nitrophenylazo" refers to a functional group or substituent obtained by substituting two hydrogen atoms on phenyl with a nitro and an azo, and positions of nitro and azo can be arbitrarily selected.

The term "benzenesulfonylazo" refers to a functional group or substituent obtained by substituting two hydrogen atoms on phenyl with a benzenesulfonic group and an azo, and positions of benzenesulfonic group and azo can be arbitrarily selected.

The term "alkoxy nitrophenyl" refers to a functional group or substituent obtained by substituting two hydrogen atoms on phenyl group with an alkoxy and an azo, and the positions of alkoxy and azo can be arbitrarily selected. The meaning of alkoxy is the same as above.

The term "phenyl" refers to a benzene-ring aryl, including substituted or unsubstituted —C$_6$H$_5$.

The term "aryl" refers to a functional group or substituent derived from simple aromatic ring; under the absence of other specification, it may either be a carbocyclic aryl group or heterocyclic aryl group containing heteroatom but not limited to N, S, O, etc.; besides, the aryl group may be a single ring or fused ring aryl; as well as a polycyclic substituent fused by aryl ring group with non-aryl ring.

The term "heteroaryl" refers to a functional group or substituent derived from aromatic ring containing heteroatoms of different number of N, S, O, or other atoms.

The term "heterocycloalkyl" refers to a cycloalkyl group including heteroatoms of different number of N, S, O, or other atoms.

The term "halophenyl" refers to a phenyl group substituted by halogen substituent, which may also have other types of substituents.

The term "polycycloalkyl" can refer to a carbocyclic aryl group, a heterocyclic aryls including but not limited to N, S, O atoms; as well as a fused ring aryl or a polycyclic substituent fused by aryl ring group with non-aryl ring.

The term "NADPH" refers to reduced nicotinamide adenine dinucleotide phosphate, or reduced coenzyme II.

The term "NADH" refers to nicotinamide adenine dinucleotide, or reduced coenzyme I.

The present invention is further illustrated by the following examples, but the following examples are not intended to limit the claims of this invention.

Example 1

The following compound was prepared:

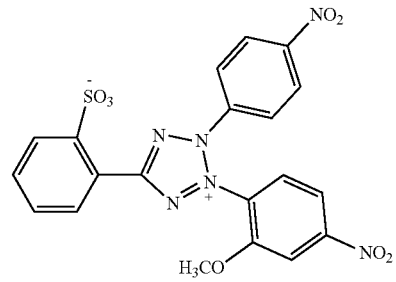

2-(4-nitrophenyl)-3-(2-methoxy-4-nitrophenyl)-5 (2-sulfonic phenyl)-2H-tetrazolium monosodium salt as EZMTT Representative Synthetic Steps:

Step A: To solution of p-nitrophenylhydrazine (6 mmol) in methanol (30 mL) we added benzaldehyde-2-sodium sulfonate (6 mmol). The mixture was stirred at the temperature of 60° C. for from 1 h to 24 h with stirring. The crude product was filtered and dried to give an orange-red solid product-benzaldehyde-2-sulfonic sodium p-nitrophenylhydrazone—with a yield of 87.1%.

Step B: To solid of 2-methoxy-4-nitroaniline (2 mmol) in the flask, we added 1 mL of water under ice-cooling, and then added 0.6 ml of concentrated hydrochloric acid, after that, added solution of NaNO2 (2.22 mmol) in water (1 mlL). The mixture was stirred for from 20 min to 5 h, and the product was 2-methoxy-4-nitroaniline diazonium salt.

Step C: To solution of benzaldehyde-2-sulfonic sodium p-nitrophenylhydrazone (2 mmol) in methanol, which was cooled to 0° C., we added 2-methoxy-4-nitroaniline diazonium salt (2 mmol) from Step B, and then added NaOH solution. The mixture was stirred for from 1 h to 24 h. The crude product was filtered, dried and separated by column chromatography to give the final product—formazan—with a yield of 87.2%.

Step D: To solution of formazan (1 mmol) from step C in methanol, we added concentrated hydrochloric acid (18 mmol) under ice-cooling, and then added hydrogen peroxide (18 mmol). The mixture was stirred for 5 h. The crude product was filtered, dried and separated by column chromatography to give a dark brownish yellow solid product—tetrazolium salt—with a yield of 33%.

$^1$H NMR (500 MHz, DMSO): δ 8.54 (d, J=8.9 Hz, 2H), 8.37 (d, J=8.8 Hz, 1H), 8.24 (d, J=8.8, 2.0 Hz 1H), 8.05 (d, J=9.4 Hz, 3H), 7.81-7.70 (m, 3H), 7.44-7.35 (m, 1H), 3.71 (s, 3H).

MP: 105° C.

FAB-MS: m/z=499[M+H]$^+$

The monosulfonic phenyltetrazole compounds of these claims, can be synthesized by suitable substrates according to the above. So long as different substrates are selected, it's possible to obtain the monosulfonic phenyltetrazole compound needed without substantially changing the preparation steps.

For example, changing the benzaldehyde-2-sulfonic sodium in this example to benzaldehyde-3-sulfonic sodium or benzaldehyde-4-sulfonic sodium, we can get the final product 2-(4-nitrophenyl)-3-(2-methoxy-4-nitrophenyl)-5 (3-sulfonic phenyl)-2H-tetrazoliummonos odium salt and 2-(4-nitrophenyl)-5 (2-methoxy-4-nitrophenyl)-5 (4-sulfonic phenyl)-2H-tetrazolium monosodium salt. The same applies to the following examples.

Example 2

The following compound was prepared based on a similar synthetic procedure in example 1 of which the substrate in step B was changed to 1-naphthylamine, and the product was a diazonium salt of 1-naphthylamine:

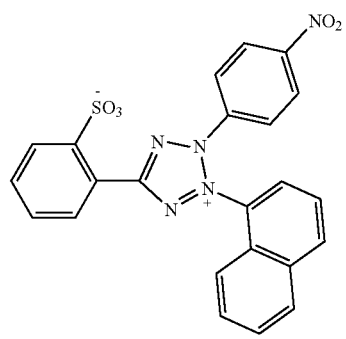

2-(4-nitrophenyl)-3-(1-naphthyl)-5 (2-disulfonic phenyl)-2H-tetrazolium monosodium salt a Black Solid, with a Yield of 47.4%

$^1$H NMR (500 MHz, DMSO): δ 8.46 (d, J=8.4 Hz, 1H), 8.29 (d, J=7.4 Hz, 1H), 8.21 (d, J=9.3 Hz 1H), 8.06 (d, J=7.9 Hz, 2H), 7.88 (d, J=9.5 Hz, 2H), 7.62 (d, J=7.8 Hz, 2H), 7.43 (t, J=7.6 Hz, 2H), 7.36 (t, J=7.4 Hz, 2H), 7.25 (d, J=6.6 Hz 2H)

MP: 102° C.

FAB-MS: m/z=429[M+H]$^+$

Example 3

The following compound was prepared based on a similar synthetic procedure in example 1 or 2 of which the substrate in step B was change to 8-aminoquinoline, and the product was a diazonium salt of 8-aminoquinoline:

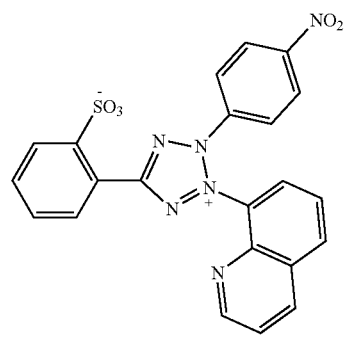

2-(4-nitrophenyl)-3-(8-quinolyl)-5 (2-sulfonic phenyl)-2H-tetrazolium monosodium salt a Black-Red Solid, with a Yield of 67.17%

$^1$H NMR (500 MHz, DMSO): δ 8.81 (d, J=4.3 Hz, 1H), 8.72 (d, J=7.8 Hz, 1H), 8.66-8.55 (m, 2H), 8.35 (d, J=9.1 Hz, 1H), 7.81 (t, J=7.6 Hz, 2H), 7.72-7.68 (m, 2H), 7.58-7.50 (m, 2H), 7.42 (d, J=6.4 Hz, 11-1), 7.36 (t, J=7.1 Hz, 1H), 7.25 (d, J=7.4 Hz, 1H)

MP: 102° C.

FAB-MS: m/z=475[M+H]$^+$

Example 4

The full-wavelength UV-visible absorption spectrum of phenyltetrazolium salt and reduced phenylformazan was shown in FIG. 1.

Wherein the phenyltetrazolium salt aforesaid was 2-(4-nitrophenyl)-3-(2-methoxy-4-nitrophenyl)-5 (2-sulfonic phenyl)-2H-tetrazolium monosodium salt synthesized in example 1.

Phenyltetrazolium salt (10 mM; almost no absorption at 450 nm; lower curve) can be reduced by NADH to orange formazan (maximum absorbance at 450 nm; Upper curve) in the presence of 1-methoxyPMS and TrispH8 (50 mM). Therefore, it can be used in the detection of NADH reductant.

Example 5

Figure 2:
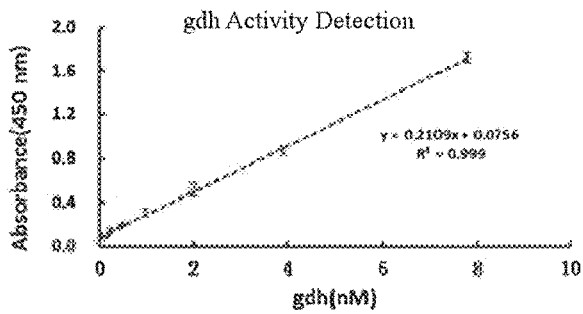
FIG. 2 shows the absorption at 450 nm of a compound with structure of monosulfonic phenyltetrazole after reacting with glutamate dehydrogenase.

Glutamate dehydrogenase activity was detected by catalytically dehydrogenating glutamic acid to produce NADPH/NADH which reduced the phenyl tetrazolium to orange Zanzan, as shown in FIG. 2.

Wherein the phenyltetrazolium salt aforesaid was 2-(4-nitrophenyl)-3-(1-naphthyl)-5 (2-sulfonic phenyl)-2H-tetrazolium monosodium salt synthesized in example 2.

Phenyltetrazolium salt had almost no absorption at 450 nm, but after reacting with 1-methoxy-5-methyl phenazine sulfate methyl ester, NADP, glutamic acid, and glutamate dehydrogenase, there was an absorption at 450 nm. Meanwhile, the intensity of light absorption was proportional to the amount of glutamate dehydrogenase.

Phenyltetrazolium salt can be used to determine the activity of glutamate dehydrogenase and drug screening Example 6

Figure 3:
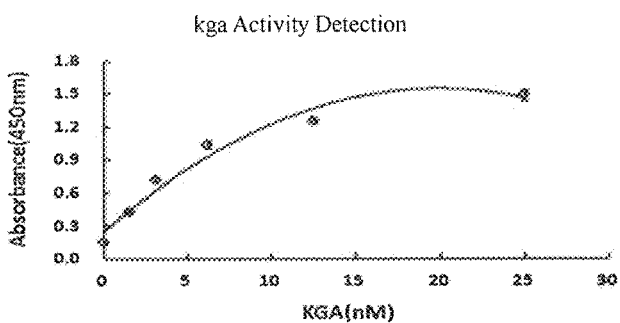
FIG. 3 shows the absorption at 450 nm of a compound with structure of monosulfonic phenyltetrazole after reacting with glutamine enzyme.

Catalytic reaction of glutaminase produced glutamic acid, which was quantified by the reaction with glutamate dehydrogenase in example 5, and the absorbance at 450 nm was shown in FIG. 3.

Phenyltetrazolium salt had almost no absorption at 450 nm; from 0.1 to 25 mMol/L of phenyltetrazolium salt reacted with 1-methyl PMS, NADP, glutamine, glutaminase, glutamate dehydrogenation enzyme in the buffer system for 2 h, and determined the absorbance of different concentrations of phenyltetrazolium substrate at 450 nm.

The intensity of the absorbed light was proportional to the amount of glutaminase.

Phenyltetrazolium salt can be used to determine the activity of glutaminase and drug screening.

Example 7

Figure 4:
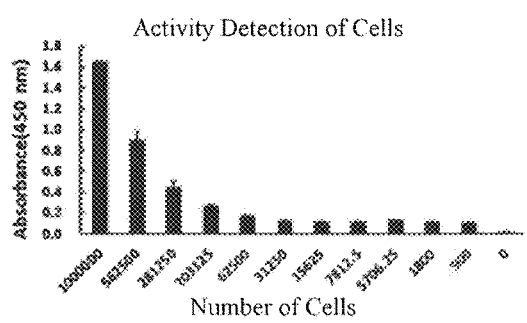
FIG. 4 shows the absorption at 450 nm of a compound with structure of monosulfonic phenyltetrazole after reacting with living cell.

After the phenyltetrazolium salt reacted with living cells, the absorbance at 450 nm was measured, as shown in FIG. 4.

Wherein the phenyltetrazolium salt aforesaid was 2-(4-nitrophenyl)-3-(8-quinolyl)-5 (2-sulfonic phenyl)-2H-tetrazolium monosodium salt synthesized in example 3.

Phenyltetrazolium salt had almost no absorption at 450 nm, but after reacting with NADH/NADPH in the cells, there was an absorption at 450 nm. Meanwhile, the intensity of light absorption was correlated with the live cell number Phenyltetrazolium salt can be used to determine the amount of viable cells.

Example 8. Comparison of EZMTT in Example 1 and WST-8

The chemical syntheses of WST-8 is a water-soluble tetrazolium salt, provided as a benzene disulfonate sodium salt of 2-(3-(2-methoxy-4-nitrophenyl)-2-(4-nitrophenyl)-2H-tetrazolium)benzene disulfonate sodium salt.

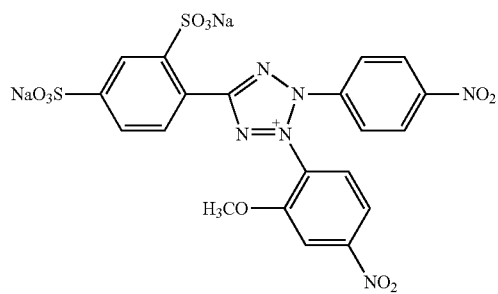

WST-8

Assay interference of tetrazolium-formazan-NAD(P)H system

To evaluate the assay interference, the tetrazolium detection reagent (WST-8 or EZMTT) in the absence or presence of 100 μM NAD(P)H was mixed with various chemicals, such as commonly used detergents (0-1% SDS, 0-0.2% Tween 20) and reducing agent (BME). The absorbance at 450 nm (reference wavelength at 620 nm) was measured to detect unusual dose response which is an indication of assay interference.

Figure 5:
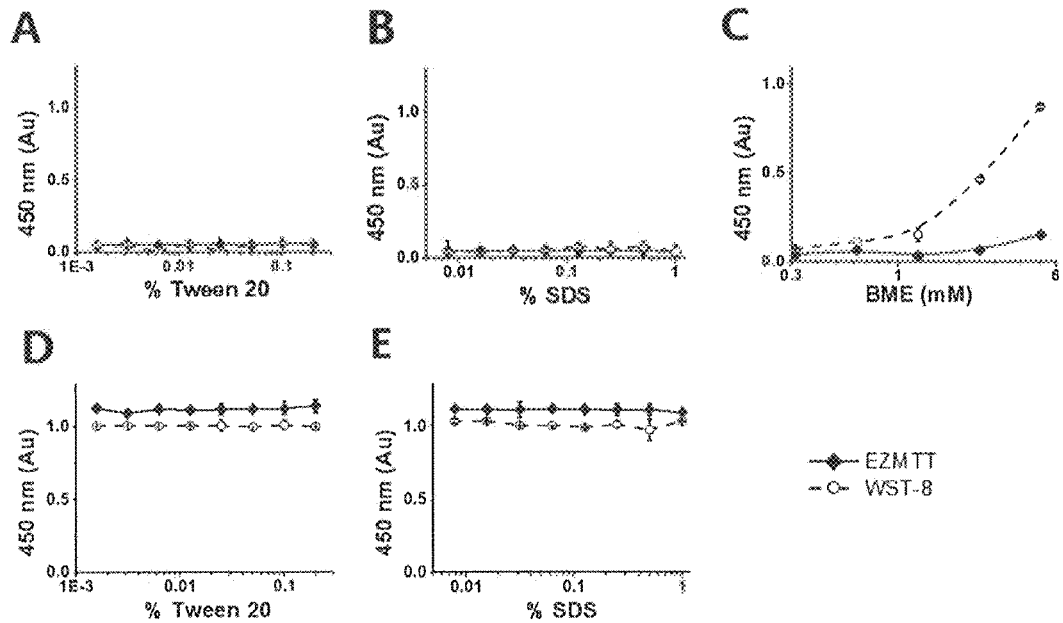
FIG. 5 shows the effects of detergents and antioxidants on the tetrazolium detection reagents. Dose response of (A) Tween 20, (B) SDS, (C) BME in the absence of NADH. Dose response of (D) Tween 20, (E) SDS in the presence of NADH.

As shown in FIG. 5, up to 0.2% Tween 20 or 1% SDS both the EZMTT and the WST-8 detection reagents showed no interference in the absence (FIG. 5A, 5B) or presence (FIG. 5D, 5E) of 100 μM NADH. However, when the antioxidant BME was tested, the WST-8 detection reagent (FIG. 5C) showed strong dose-dependent false positive signals, whereas the EZMTT reagent showed essentially no signal changes.

Reagent Stability Assays

The tetrazolium detection reagent (WST-8 or EZMTT) was stored at 4 and −20° C., respectively. Once a month, the stored tetrazolium detection reagent was tested using 100 μM NADH in 50 mM Tris-Cl (pH 8) and the response was measured at 450 nm.

Figure 6:
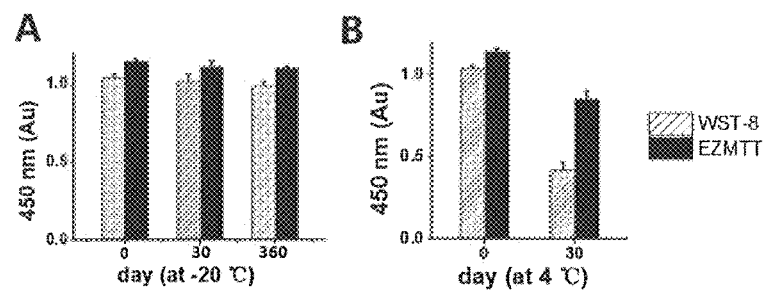
FIG. 6 shows the stability of the WST-8 or EZMTT detection reagents at −20□ and 4□.

For the stability test, the WST-8, EZMTT detection reagents were stored at 4° C. and −20° C. up to a year. Both reagents were tested in NADH titration every month for their activities. As shown in FIG. 6A, storage at −20° C., WST-8 or EZMTT solution showed essentially no changes in activity for up to a year. However, after storage at 4° C. for a month, EZMTT is relatively more stable and lost activity only by 25% (FIG. 6B), whereas WST-8 lost activity by 60%. These results indicated that EZMTT detection reagent is more stable than the WST-8 reagents and suitable for dehydrogenase or cell-based inhibitor screening assay.

E. coli GDH Activity Assay

To GDH (0-8 nM final), a mixture of NADP$^+$ (100 μM), glutamate (5 mM) and the EZMTT detection reagent in 50 mM Tris-Cl (pH 8) was added, and the UV absorbance changed at 450 nm and were measured every 2 min to determine initial velocity. E. coli GDH (4 nM) showed linear initial velocity for an over 2 h assay period. The $K_m$ for NAD or NADP was measured by mixing dilutions of NAD(P)$^+$ (0-10 mM), 5 mM glutamate and the tetrazolium detection reagent (0.5 mM EZMTT, 10 μM 1-methoxy PMS) in 50 mM Tris-Cl (pH 8; 100 μl), and the reactions were initiated after the addition of GDH (4 nM). The UV absorbance at 450 nm was measured every 2 min to obtain the initial velocity.

Figure 7:
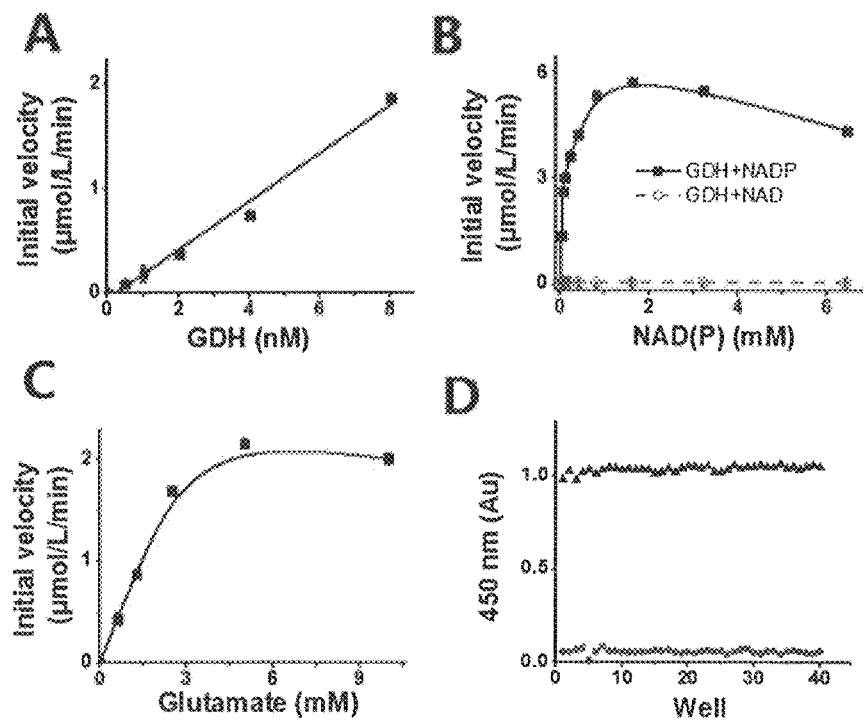
FIG. 7 shows Kinetics study and GDH assay evaluation. (A) The assay showed linear dose response to *E. coli* GDH; (B) NADP substrate inhibition was observed for *E. coli* GDH at high concentration, but NAD is not a substrate for E. coli GDH; (C) Maximum initial velocity was observed with 5 mM glutamate in the presence of 100 µM NADP. (D) Assay reproducibility measurement for EZMTT regents (Z factor 0.9).

GDH catalyzes the reversible oxidative deamination of glutamate to form 2-oxoglutarate and free $NH_4^+$, and at the same time converts the NAD(P)$^+$ to NAD(P)H. The resulting NAD(P)H can be measured by the EZMTT detection reagent as an indication for GDH activity. As shown in FIG. 7A, the recombinant E. coli GDH with a N-terminal His$_6$ tag demonstrated linear initial velocity and the linear dose response (r=0.99) in the presence of up to 16 nM GDH enzyme indicating high enzymatic activity. E. coli GDH used NADP as the cofactor and showed substrate inhibition at high NADP concentration (FIG. 7B) similar to that of the GDH in mouse liver;

however, E. coli GDH showed no enzymatic activity if NAD was used as a cofactor. Since E. coli GDH showed strong NADP substrate inhibition, we measured its glutamate (0-25 mM) dose response in the presence of 100 μM NADP, and the $V_m$ was reached at 5 mM glutamate concentration (FIG. 7C). Using 4 nM GDH, 100 μM NADP and 5 mM glutamate in E. coli GDH activity assay, we obtained linear initial velocity that last up to 2 h of reaction time.

Further, using 4 nM E. coli GDH as a positive control and no GDH as a negative control, we observed excellent assay reproducibility with a Z factor of 0.9 (FIG. 7D), indicating that the assay is suitable for inhibitor screening.

In conclusion, the foregoing examples are preferred embodiments of the present invention, it will be appreciated that modification can be made without departing from the spirit of the invention. Such modifications are intended to fall within the scope of the appended claims.

The invention claimed is:

1. A composition of Monosulfonic phenyltetrazole compounds which are selected from the following compounds:

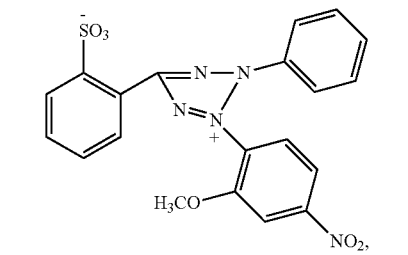

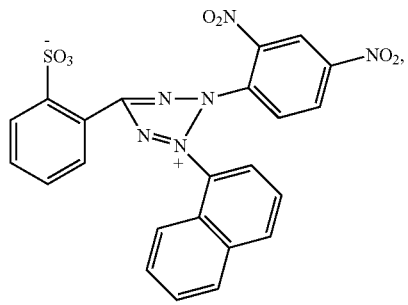

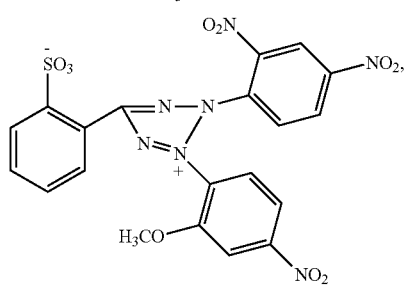

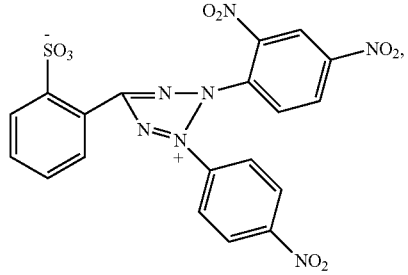

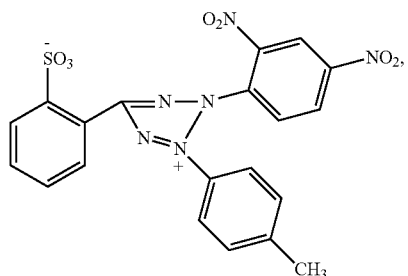

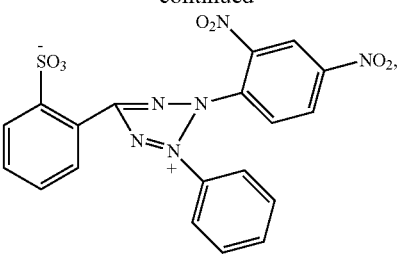

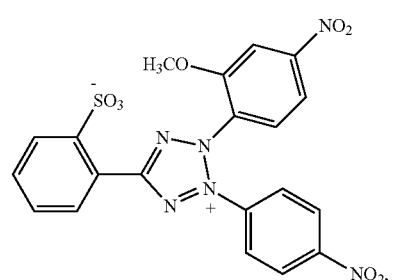

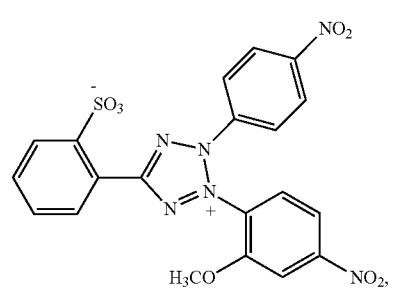

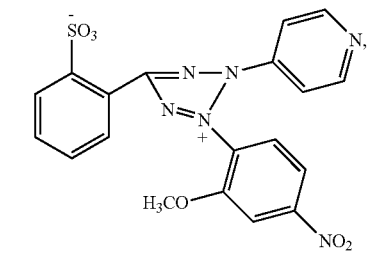

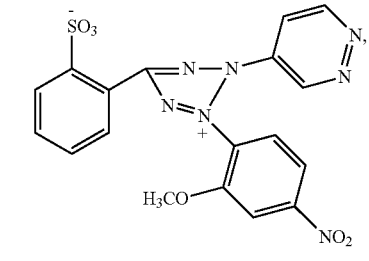

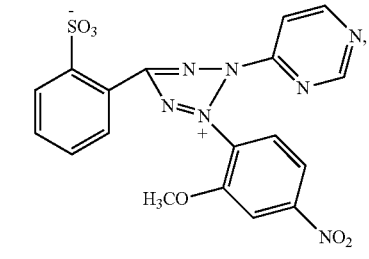

-continued
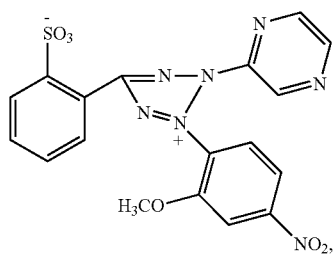
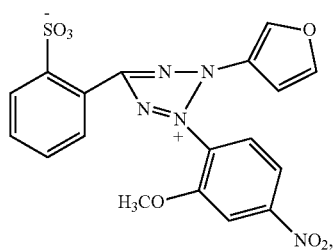
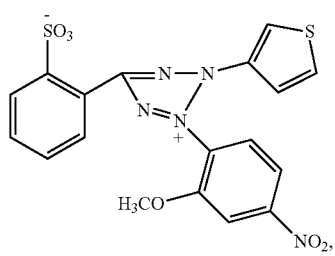
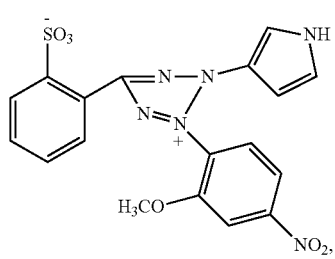
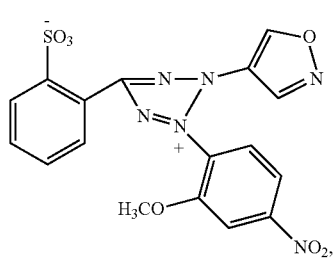
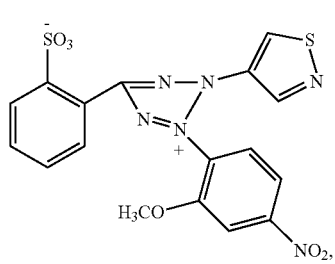
-continued
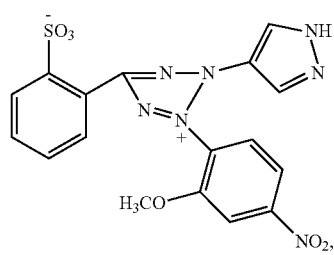
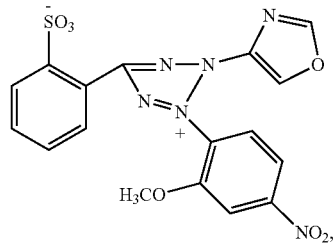
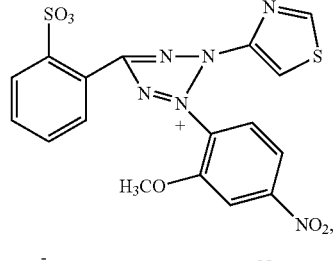
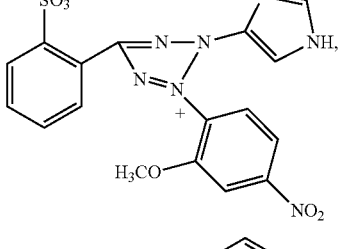
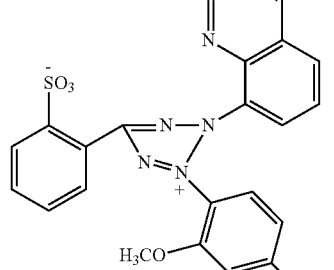
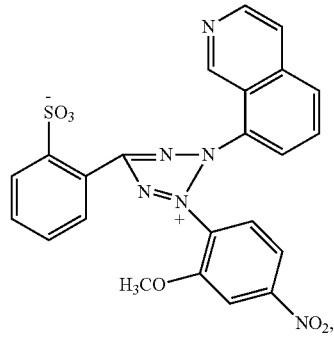

23
-continued
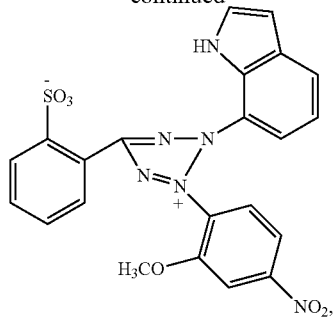
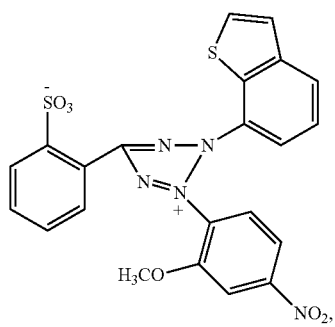
24
-continued
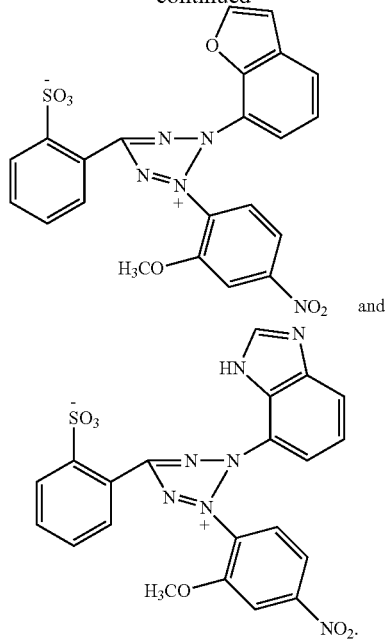
* * * * *